US012594274B2

(12) United States Patent
Björklund

(10) Patent No.: US 12,594,274 B2
(45) Date of Patent: Apr. 7, 2026

(54) METHOD FOR PREPARING A CRYSTALLINE FORM OF RABEXIMOD

(71) Applicant: Cyxone AB, Malmö (SE)

(72) Inventor: Ulf Björklund, Uppsala (SE)

(73) Assignee: Gulch Pharma AB, Sollentuna (SE)

( * ) Notice: Subject to any disclaimer, the term of this patent is extended or adjusted under 35 U.S.C. 154(b) by 527 days.

(21) Appl. No.: 18/000,943

(22) PCT Filed: Jun. 10, 2021

(86) PCT No.: PCT/EP2021/065694
§ 371 (c)(1),
(2) Date: Dec. 7, 2022

(87) PCT Pub. No.: WO2021/250197
PCT Pub. Date: Dec. 16, 2021

(65) Prior Publication Data

US 2023/0227455 A1 Jul. 20, 2023

(30) Foreign Application Priority Data

Jun. 10, 2020 (EP) .................................... 20179239
Jun. 10, 2020 (EP) .................................... 20179277
(Continued)

(51) Int. Cl.
*A61K 31/4985* (2006.01)
*A61K 9/00* (2006.01)
(Continued)

(52) U.S. Cl.
CPC ........ *A61K 31/4985* (2013.01); *A61K 9/0053* (2013.01); *A61K 9/4808* (2013.01);
(Continued)

(58) Field of Classification Search
CPC .............. A61K 31/4985; A61K 9/0053; A61K 9/4808; A61P 19/02; C07D 487/04; A07B 2200/13
See application file for complete search history.

(56) References Cited

U.S. PATENT DOCUMENTS 4,990,510 A 2/1991 Bergman
6,248,742 B1 6/2001 Bergman et al.
(Continued)

FOREIGN PATENT DOCUMENTS

CN 102115457 A 7/2011
CN 105061432 A 11/2015
(Continued)

OTHER PUBLICATIONS

Ashry, E., et al., Microwave irradiation for enhancing the regioselective synthesis of 6H-indolo[2,3-b]quinoxalines, Journal of Chemical Research, 2005(4):229-232, Apr. 2005.
(Continued)

*Primary Examiner* — Brandon J Fetterolf
(74) *Attorney, Agent, or Firm* — Weston R. Gould; Dinsmore & Shohl LLP

(57) ABSTRACT

The present invention relates to a process for preparing 9-Chloro-2,3-dimethyl-6-(N,N-dimethylaminoethylamino-2-oxoethyl)-6H-indolo-[2,3-b]quinoxaline, wherein said process is suitable for large scale synthesis.

17 Claims, 2 Drawing Sheets

(30) Foreign Application Priority Data

Jun. 10, 2020 (EP) .................................... 20179279
Jun. 18, 2020 (EP) .................................... 20180706

(51) Int. Cl.
*A61K 9/48* (2006.01)
*A61P 19/02* (2006.01)
*C07D 487/04* (2006.01)

(52) U.S. Cl.
CPC ........... *A61P 19/02* (2018.01); *C07D 487/04* (2013.01); *C07B 2200/13* (2013.01)

(56) References Cited

U.S. PATENT DOCUMENTS

| | | | |
|---|---|---|---|
| 6,333,327 B2 | | 12/2001 | Moller et al. |
| 7,589,093 B2 | * | 9/2009 | Bergman et al. |
| 11,278,499 B2 | | 3/2022 | Li |
| 2005/0288296 A1 | | 12/2005 | Bergman et al. |

FOREIGN PATENT DOCUMENTS

| | | | |
|---|---|---|---|
| EP | 1261344 | | 12/2002 |
| EP | 1756111 | | 2/2007 |
| JP | H8-165278 | A | 6/1996 |
| JP | 2008-502676 | A | 1/2008 |
| WO | WO200160371 | | 8/2001 |
| WO | WO2004048335 | A2 | 6/2004 |
| WO | WO2005123741 | | 12/2005 |
| WO | WO2014140321 | | 9/2014 |
| WO | WO2021250196 | | 12/2021 |
| WO | WO2021250197 | | 12/2021 |
| WO | WO2021250199 | | 12/2021 |
| WO | WO2021250204 | | 12/2021 |

OTHER PUBLICATIONS

Bansback, et al., How important is Mode of Administration in Treatments for Rheumatic Diseases and Related Conditions?, Curr Rheumatol Rep, 23: 1-13, Apr. 2015.
Berge, et al., Pharmaceutical Salts, Journal of Pharmaceutical Sciences, 1: 1-19, Jan. 1977.
Gould, Phillip, Salt selection for basic drugs, International Journal of Pharmaceutics, 33: 201-217, 1986.
Huftqvist, et al., Rabeximod reduces arthritis severity in mice by decreasing activation of inflammatory cells, Ann Rheum Dis., 69: 1527-1532, 2010.
Lambert, et al., Dose Escalation of Parenteral Methotrexate in Active Rheumatoid Arthritis That Has Been Unresponsive to Conventional Doses of Methotrexate, Arthritis & Rheumatism, 50,(2): 364-371, Feb. 2004.
Paulekuhn, et al., Salt screening and characterization for poorly soluble, weak basic compounds: case study albendazole, Pharmazie, 68: 555-564, 2013.
Stieger, et al., Recrystallization of Active Pharmaceutical Ingredients, Crystallization—Science and Technology, 183-204, 2006.
Ivaschenko, A. et al., Khimiya Geterotsiklicheskikh Soedinenii, vol. 5,pp. 667-672, 1984.
Sanchez, J. et al., An Efficient Synthesis of 6-Formyl-1,2-dihydro-2-oxo-3-pyridinecarboxylic Acid and some Carbonyl Derivatives of it and its 6-Acetyl Homologue, Journal of Heterocyclic Chemistry, 31: 297-303, 1994.
http:\\www.msakc.org/Articles/MSPain.htm; last accessed Jun. 20, 2008.
Hultqvist et al. "The novel small molecule drug Rabeximod is effective in reducing disease severity of mouse models of autoimmune diseases", Ann Rheum Dis, 68, 2009; pp. 130-135.
OxyPharma, "Study to Evaluate the Efficacy and Saftey of the Orally Administrated Rob 803 When Added to Methotrexate (ROBUST)," Clinical Trails, Aug. 21, 2009, 1-6.
Visser and van der Heijde, "Optimal dosage and route of administration of methotrexate in rheumatoid arthritis: a systematic review of the literature", Annals of the rheumatic diseases, 68, 7, 2009; pp. 1094-1099.
Westman et al., "Suppressive effects of a quinoxaline-analouge (Rob 803) on pathogenic immune mechanisms in collagen-induced arthritis", British Society for Immunology, Clinical and Experimental Immunology, 152, Jan. 15, 2008; pp. 192-199.
Beigel JH, et al. Avian influenza A (H5N1) infection in humans. N Engl J Med., 2005;353(13):1374-1385.
Billack B., Macrophage activation: role of toll-like receptors, nitric oxide, and nuclear factor kappa B, Am J Pharm Educ., 2006;70(5):102.
Byrn, et al., "Pharmaceutical Solids: A Strategic Approach to Regulatory Considerations" Pharmaceutical Research, vol. 12, No. 7, p. 945-954, 1995.
Cheung CY, et al., Induction of proinflammatory cytokines in human macrophages by influenza A (H5N1) viruses: a mechanism for the unusual severity of human disease?, Lancet, 2002;360(9348):1831-1837.
Corman VM, et al., Detection of 2019 novel coronavirus (2019-nCOV) by real-time RT-PCR, Euro Surveill., 2020;25(3):2000045.
Florence, et al., "Polymorph screening in pharmaceutical development", European Pharmaceutical Review, Aug. 19, 2010; pp. 1-14.
Giusti, et al., "The novel anti-rheumatic compound Rabeximod impairs differentiation and function of human pro-inflammatory dendritic cells and macrophages," Immunobiology, 216, p. 243-250, 2016.
Guamer J, et al., Pathology and pathogenesis of bioterrorism-related inhalational anthrax, Am J Pathol., 2003;163(2):701-709.
Haeberle HA, et al., Respiratory syncytial virus-induced activation of nuclear factor-kappaB in the lung involves alveolar macrophages and toll-like receptor 4-dependent pathways, J Infect Dis., 2002;186(9):1199-1206.
Harbecke O, et al., The synthetic non-toxic drug 2,3-dimethyl-6(2-dimethylaminoethyl)-6H-indolo-(2,3-b)quinoxaline inhibits neutrophil production of reactive oxygen species, J Leukoc Biol., 1999;65(6):771-777.
Harmenberg J, et al., The mechanism of action of the anti-herpes virus compound 2,3-dimethyl-6(2-dimethylaminoethyl)-6H-indolo-(2,3-b)quinoxaline. Antiviral Res, 1991;15(3):193-204.
Harmenberg J, et al., Antiherpesvirus activity and mechanism of action of indolo-(2,3-b)quinoxaline and analogs. Antimicrob Agents Chemother., 1988;32(11):1720-1724.
Hemmi H, et al., A Toll-like receptor recognizes bacterial DNA. Nature. 2000;408(6813):740-745.
Hendershott, C.H., Processing of the American Society of Horticultural Science, (1964), 85, 201-9.
Lee, Eun Hee, "A practical guide to pharmaceutical polymorph screening & selection", Asian Journal of Pharmaceutical Science, 9, p. 163-175, 2014.
Lew TW, et al., Acute respiratory distress syndrome in critically ill patients with severe acute respiratory syndrome. JAMA., 2003;290(3):374-380.
McGonagle D, et al., The Role of Cytokines including Interleukin-6 in COVID-19 induced Pneumonia and Macrophage Activation Syndrome-Like Disease, Autoimmun Rev, 2020;19(6):102537.
Peiris JS, et al., Re-emergence of fatal human influenza A subtype H5N1 disease, Lancet. 2004;363(9409):617-619.
Schiaffino, and Cea, "Assessing Chronic Illness Representations: The Implicit Models of Illness Questionnaire" Journal of Behavioral Medicine, vol. 18, No. 6. 1995, pp. 531-548.
Serajuddin, Abu T.M., "Salt formation to improve drug solubility," Advanced Drug Delivery Reviews, 59, p. 603-616, May 29, 2007.
Bowker and Stahl, "Preparation of Water-Soluble Compounds Through Salt Formation," The Practice of Medicinal Chemistry, 35, p. 601-615, 2003.
Stahl, P. Heinrich, "Handbook of Pharmaceutical Salts Properties, Selection, and Use" international Union of Pure and Applied Chemistry (IUPAC), 2002.
Tumpey TM, et al., Characterization of the reconstructed 1918 Spanish influenza pandemic virus, Science, 2005;310(5745):77-80.
Westman, et al, "Suppressive effects of a quinoxaline-analogue (Rob 803) on pathogenic immune mechanisms in collagen-induced

(56) References Cited

OTHER PUBLICATIONS arthritis," British Society for Immunology, Clinical and Experimental Immunology, 152: 192-199, 2008.
Van Riel D, et al., H5N1 Virus Attachment to Lower Respiratory Tract, Science, 2006;312(5772):399.
Zawadoski, et al, "Synthesis of some 6-subsitituted derivatives of indophenazine with potential pharmacological activity", Acta Poloniae Pharmaceutica, vol. 52, No. 3, pp. 249,51 (1995).

* cited by examiner

METHOD FOR PREPARING A CRYSTALLINE FORM OF RABEXIMOD

CROSS REFERENCE TO RELATED APPLICATIONS

This application is a U.S. National Stage under 35 U.S.C. § 371 of PCT/EP2021/065694 filed Jun. 10, 2021, which depends from and claims priority to European application number 20180706.2 filed Jun. 18, 2020, European application number 20179279.3 filed Jun. 10, 2020, European application number 20179239.7 filed Jun. 10, 2020, and European application number 20179277.7 filed Jun. 10, 2020 the entire contents of each of which are incorporated herein by reference.

TECHNICAL FIELD

The present invention relates to a process of preparing 9-Chloro-2,3-dimethyl-6-(N,N-dimethylaminoethylamino-2-oxoethyl)-6H-indolo-[2,3-b]quinoxaline (rabeximod), wherein said process is suitable for large scale synthesis. The process parameters are stable, and the process is suitable for GMP.

BACKGROUND ART

The compound rabeximod has been described in European patent application publication EP1756111A1 later granted as EP1756111B1. The preparation of rabeximod, as compound E, is specifically described in EP1756111A1 as a small-scale process without any description on how to develop a process that can be used for GMP and upscaled. Rabeximod was made in a 58% yield in a small-scale lab process, but no parameters for scaling up have been disclosed.

The objective of the present invention is to provide a process that is suitable for large scale synthesis in good yield, with stable process parameters, and suitable for GMP production.

SUMMARY OF THE INVENTION

The present invention relates to a new process for preparing 9-Chloro-2,3-dimethyl-6-(N,N-dimethylaminoethylamino-2-oxoethyl)-6H-indolo-[2,3-b]quinoxaline also known as rabeximod, which process can be scaled up to large scale and/or industrial scale such as 10 kg or higher. The process can also be used for smaller scale such as from 200 g to 10 kg.

Further objects and advantages of the present invention will appear from the following description, and claims.

DESCRIPTION OF THE INVENTION

The compound known under the INN 'rabeximod' has the IUPAC name 9-Chloro-2,3-dimethyl-6-(N,N-dimethylaminoethylamino-2-oxoethyl)-6H-indolo-[2,3-b]quinoxaline and has the following molecular structure.

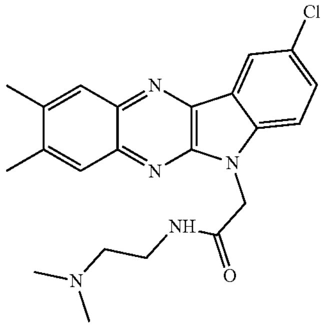 [SMILES: Cc1cc2nc3c4cc(Cl)ccc4n(CC(=O)NCCN(C)C)c3nc2cc1C]

Throughout the application the terms "Rabeximod", "rabeximod" or "9-Chloro-2,3-dimethyl-6-(N,N-dimethylaminoethylamino-2-oxoethyl)-6H-indolo-[2,3-b]quinoxaline" are used interchangeable and mean the compound in any solid form or liquid form unless otherwise indicated or implied under the given circumstances.

In a first aspect the present invention relates to a process for preparing 9-Chloro-2,3-dimethyl-6-(N,N-dimethylaminoethylamino-2-oxoethyl)-6H-indolo-[2,3-b]quinoxaline (Rabeximod) or a salt thereof, which process is suitable for large scale production/synthesis, wherein the process comprises the step of:

reacting a solution or suspension of 9-chloro-2,3-dimethyl-6H-Indolo[2,3-b] quinoxaline in the presence of an aqueous base sufficiently strong to deprotonize the indole N—H and optionally a catalyst, with 2-Chloro-N-(2-dimethylaminoethyl)acetamide or a salt thereof to obtain Rabeximod or a salt thereof.

In one embodiment, the catalyst is present. When present, the catalyst is typically an alkaline halogen-based catalyst, e.g. KI (potassium iodide).

In a further embodiment, 9-chloro-2,3-dimethyl-6H-Indolo[2,3-b] quinoxaline or a salt thereof is dissolved in an organic solvent. Typically, such solvent is a water-miscible organic solvent, such as a polar water-miscible organic solvent, such as a polar aprotic water-miscible organic solvent, such as a cyclic ether, e.g. THF. Typical embodiments are selected from one or more of acetonitrile, isopropylacetate, ethylacetate, THF and toluene, optionally mixed with water.

In a still further embodiment, 2-Chloro-N-(2-dimethylaminoethyl) acetamide or a salt thereof is dissolved in an organic solvent, such as a water-miscible organic solvent, such as a polar water-miscible organic solvent. Typically, such as a polar aprotic water-miscible organic solvent, such as a cyclic ether, e.g. THF.

During the process, 2-Chloro-N-(2-dimethylaminoethyl) acetamide may be used as the free base or a salt. In a further embodiment the 2-Chloro-N-(2-dimethylaminoethyl) acetamide is a salt, and preferably the hydrochloride salt. In another embodiment 2-Chloro-N-(2-dimethylaminoethyl) acetamide is used as the free base.

As described above, the process involves the use of an aqueous base, and typically the aqueous base is an alkaline based base, such as aqueous KOH or NaOH. Preferably, the base is aqueous NaOH, such as a 50% NaOH aqueous solution.

In a further embodiment, the reaction takes place under an inert gas, e.g. nitrogen gas or argon gas, at atmospheric pressure. Preferably, the inert gas is nitrogen gas.

In a still further embodiment, about 1 molar equivalent 9-chloro-2,3-dimethyl-6H-Indolo[2,3-b] quinoxaline is deprotonized with at least about 2 volumes of the aqueous base. Typically, about 8 equivalents (in relation to 9-chloro-2,3-dimethyl-6H-Indolo[2,3-b] quinoxaline) of the aqueous base are used. Preferably, 9-chloro-2,3-dimethyl-6H-Indolo [2,3-b] quinoxaline and the aqueous base are mixed at a suitable temperature, such as about 50-65° C., until a clear solution is formed, such as up to about 1 hour or more. It is preferred that the solvent, such as THF, has dissolved all of the 9-chloro-2,3-dimethyl-6H-Indolo[2,3-b] quinoxaline, since the yield increases.

Preferably, the catalyst is present. In an embodiment, the catalyst in a suitable amount is added under vigorous stirring and mixed for about 10 to 60 minutes at a suitable temperature, such as about 50-65° C. The suitable amount of the catalyst should be sufficient to carry out the catalytic effect and may be from about 0.5 to 1.5 molar equivalents. For instance, KI is typically used in an amount of about 0.7-0.9 molar equivalents.

In a still further embodiment, 2-Chloro-N-(2-dimethylaminoethyl) acetamide or a salt thereof is added to the solution, such as THF solution, of 9-chloro-2,3-dimethyl-6H-Indolo[2,3-b] quinoxaline in the aqueous base and mixed for at least about 1 hour, such as at least about 2 hours, at a suitable temperature, such as about 50-65° C. Preferably, 2-Chloro-N-(2-dimethylaminoethyl) acetamide is added in an amount of about 1-3, such as about 2, molar equivalents.

The Rabeximod compound can be purified according to known techniques, or as described here after and/or in the experimental section. In a preferred embodiment Rabeximod is purified and isolated as the free base, such as a crystalline free base.

In a further aspect the present invention relates to a crystalline free base of Rabeximod. Preferably, the crystalline free base of Rabeximod has a melting point of 259-261° C. A crystalline free base of Rabeximod is also identified by the XRPD diffractogram, DSC and X-ray shown in FIGS. 1 and 2. The crystalline free base of Rabeximod was isolated in high purity as measured by HPLC above 98%, thus in a further embodiment the crystalline free base of Rabeximod is an isolated free base having a purity above 98%.

The crystalline rabeximod free base compound is suitable for further processing into a solid oral dosage composition for treatment of autoimmune diseases, such as rheumatoid arthritis and/or multiple sclerosis.

In a further embodiment the present process comprises the preceding step of:

reacting a solution or suspension of 4,5-Dimethyl-1,2-phenylenediamine with 5-chloroisatin under acidic conditions at elevated temperatures up to reflux to obtain 9-chloro-2,3-dimethyl-6H-Indolo[2,3-b] quinoxaline or a salt thereof.

In a still further embodiment the present process comprises the preceding step of:

reacting a solution or suspension of Chloroacetyl chloride with N,N-Dimethylethylene diamine to obtain 2-Chloro-N-(2-dimethylaminoethyl)acetamide or a salt thereof.

Preferably, the process of the present invention for preparing Rabeximod comprises both the preceding steps of:

reacting a solution or suspension of 4,5-Dimethyl-1,2-phenylenediamine with 5-chloroisatin under acidic conditions at elevated temperatures up to reflux to obtain 9-chloro-2,3-dimethyl-6H-Indolo[2,3-b] quinoxaline or a salt thereof, and reacting a solution or suspension of Chloroacetyl chloride with N,N-Dimethylethylene diamine to obtain 2-Chloro-N-(2-dimethylaminoethyl)acetamide or a salt thereof.

In a still further aspect, the present invention concerns a process for preparing 9-chloro-2,3-dimethyl-6H-Indolo[2,3-b] quinoxaline, which process is suitable for large scale production/synthesis, wherein the process comprises the step of:

reacting a solution or suspension of 4,5-Dimethyl-1,2-phenylenediamine with 5-chloroisatin under acidic conditions at elevated temperatures up to reflux to obtain 9-chloro-2,3-dimethyl-6H-Indolo[2,3-b] quinoxaline.

The embodiments as described below are independently embodiments for both the process of preparing Rabeximod or a salt thereof and the process of preparing 9-chloro-2,3-dimethyl-6H-Indolo[2,3-b] quinoxaline or a salt thereof.

In a further embodiment, the acidic condition is an organic acid, such as a C2-C5 carboxylic acid, typically acetic acid.

In a still further embodiment, 4,5-Dimethyl-1,2-phenylenediamine and 5-chloroisatin are both dissolved in the acid before the reaction.

In a further embodiment, the acid is in surplus, such as at least 2 volumes, such as at least 4 volumes. Typically, the acid is in at least 4 volumes surplus for 4,5-Dimethyl-1,2-phenylenediamine and at least 10 volumes surplus for 5-chloroisatin.

In a still further embodiment, the elevated temperature is reflux temperature.

In a further embodiment, 4,5-Dimethyl-1,2-phenylenediamine or a salt thereof is dissolved in the acid before reaction with 5-chloroisatin and 5-chloroisatin or a salt thereof is dissolved in the acid before reaction with 4,5-Dimethyl-1,2-phenylenediamine.

In a still further embodiment, 4,5-Dimethyl-1,2-phenylenediamine is added in an amount of about 1-3, such as about 1-2, e.g. about 1.1, molar equivalents.

In a further embodiment, 5-chloroisatin is added in an amount of about 1-3, such as about 1-2, e.g. about 1, molar equivalents.

In a still further embodiment, dissolved 4,5-Dimethyl-1,2-phenylenediamine is added to dissolved 5-chloroisatin under reflux temperature. Typically, 4,5-Dimethyl-1,2-phenylenediamine is added to 5-chloroisatin over at least about 2 hours, such as from 2-4 hours, under reflux temperature.

In a further embodiment the acid is distilled from the reaction mixture and additional acid is added at a similar rate during the distillation. Typically, the reaction mixture, after distillation, is stirred at reflux temperature for at least about 1 hour, such as about 2 hours.

In a still further embodiment, 9-chloro-2,3-dimethyl-6H-Indolo[2,3-b] quinoxaline is purified and isolated as the free base.

In a further aspect, the present invention relates to 9-chloro-2,3-dimethyl-6H-Indolo[2,3-b] quinoxaline as a solid, such as a crystalline free base.

In a further aspect the present invention relates to a process for preparing 2-Chloro-N-(2-dimethylaminoethyl) acetamide or a salt thereof, which process is suitable for large scale production/synthesis, wherein the process comprises the step of:

reacting a solution or suspension of Chloroacetyl chloride with N,N-Dimethylethylene diamine to obtain 2-Chloro-N-(2-dimethylaminoethyl)acetamide or a salt thereof.

The embodiments as described below are independently embodiments for both the process of preparing Rabeximod or a salt thereof and the process of preparing 2-Chloro-N-(2-dimethylaminoethyl) acetamide or a salt thereof.

In an embodiment, chloroacetyl chloride is dissolved in an organic solvent, such as an organic ester, such as a C4 to C6 ester, such as ethyl acetate.

In a further embodiment, N,N-Dimethylethylene diamine is dissolved in an organic solvent, such as an organic ester, such as a C4 to C6 ester, such as ethyl acetate.

In a still further embodiment, Chloroacetyl chloride and N,N-Dimethylethylene diamine are both dissolved before the reaction.

In a further embodiment, N,N-dimethylethylene diamine in solution is added to Chloroacetyl chloride in solution at a rate keeping the temperature in the solution below about 30° C.

In a still further embodiment, N,N-dimethylethylene diamine or a salt thereof is dissolved in the solvent before reaction with Chloroacetyl chloride and 5 Chloroacetyl chloride or a salt thereof is dissolved in the solvent before reaction with N,N-dimethylethylene diamine.

In a further embodiment, the solvent is in surplus in relation to Chloroacetyl chloride, such as at least about 2 volumes, such as at least about 4 volumes.

In a still further embodiment, the solvent is in equivalent or volume surplus in relation to N,N-Dimethylethylene diamine, such as in equivalent ratio.

In a further embodiment, Chloroacetyl chloride is added in an amount of about 1-3, such as about 1-2, e.g. about 1, molar equivalents.

In a still further embodiment, N,N-dimethylethylene diamine is added in an amount of about 1-3, such as about 1-2, e.g. about 1, molar equivalents.

In a further embodiment, 2-Chloro-N-(2-dimethylamino-ethyl) acetamide or a salt thereof is purified and isolated as a salt thereof, such as the HCl salt.

In a preferred embodiment rabeximod obtained using the process described herein, is purified by consecutive steps of dissolving the crude reaction product in a water-miscible organic solvent, such as a polar water-miscible organic solvent, such as a polar aprotic water-miscible organic solvent, such as a cyclic ether, typically tetrahydrofuran, water, and an acid, such as a hydro halogenid, typically HCl mixture, filtering and heating to above 35° C., preferably to about 50° C., adjusting pH to at least 9, typically to a value within the range of 10-12, by addition of an aqueous base, typically NaOH, cooling to a temperature of between 18 and 25° C. and diluting with water, stirring for at least 10 hours, typically at least 12 hours, filtering, typically at 20 to 25° C., and washing, typically on the filter, with a water-miscible organic solvent, such as a polar water-miscible organic solvent, such as a polar aprotic water-miscible organic solvent, such as a cyclic ether, typically tetrahydrofuran and water mixture, to provide purified rabeximod crystalline free base. If desired, pharmaceutically acceptable salts can be made from a solution of the crystalline free base of rabeximod.

In a particular embodiment, a process for preparing 9-Chloro-2,3-dimethyl-6-(N,N-dimethylaminoethylamino-2-oxoethyl)-6H-indolo-[2,3-b]quinoxaline (Rabeximod) or a salt thereof, as defined herein is provided, said process comprising the steps of:

a) reacting a solution or suspension of 4,5-Dimethyl-1,2-phenylenediamine with 5-chloroisatin under acidic conditions at elevated temperatures up to reflux to obtain 9-chloro-2,3-dimethyl-6H-Indolo[2,3-b] quinoxaline or a salt thereof;
b) reacting a solution or suspension of Chloroacetyl chloride with N,N-Dimethylethylene diamine to obtain 2-Chloro-N-(2-dimethylaminoethyl)acetamide or a salt thereof;
c) reacting a solution or suspension of 9-chloro-2,3-dimethyl-6H-Indolo[2,3-b] quinoxaline as obtained in step a) in the presence of an aqueous base sufficiently strong to deprotonize the indole N—H and optionally a catalyst, with 2-Chloro-N-(2-dimethylaminoethyl)acetamide or a salt thereof as obtained in step b), so as to obtain rabeximod or a salt thereof; and
d) subjecting the rabeximod or salt thereof as obtained in step c) to one or more purification steps, preferably to the purification procedure as defined herein before.

As will be apparent to the person skilled in the art, based on the present disclosure, steps a) and b) in the above process can be (and typically are) carried out independently and in any order or sequence, including simultaneously.

A further aspect of the present invention relates to a rabeximod compound that is obtainable by any one of the processes as defined herein.

Further embodiments of the process are described in the experimental section herein, and each individual process as well as each starting material constitutes embodiments that may form part of embodiments.

The term "and/or" as used herein is intended to mean both alternatives as well as each of the alternatives individually. For instance, the expression "xxx and/or yyy" means "xxx and yyy"; "xxx"; or "yyy", all three alternatives are subject to individual embodiments.

The above embodiments should be seen as referring to any one of the aspects (such as 'crystalline free base of Rabeximod' and/or 'process suitable for large scale synthesis for preparing rabeximod') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

NUMBERED EMBODIMENTS OF THE INVENTION

1. A process for preparing 9-Chloro-2,3-dimethyl-6-(N,N-dimethylaminoethylamino-2-oxoethyl)-6H-indolo-[2,3-b]quinoxaline (Rabeximod) or a salt thereof, wherein the process comprises the step of:

reacting a solution or suspension of 9-chloro-2,3-dimethyl-6H-Indolo[2,3-b] quinoxaline in the presence of an aqueous base sufficiently strong to deprotonize the indole N—H and optionally a catalyst, with 2-Chloro-N-(2-dimethylaminoethyl)acetamide or a salt thereof to obtain Rabeximod or a salt thereof.

2. The process of embodiment 1, wherein the catalyst is present.
3. The process of any one of embodiments 1-2, wherein 9-chloro-2,3-dimethyl-6H-Indolo[2,3-b] quinoxaline or a salt thereof is dissolved in an organic solvent.
4. The process of any one of embodiments 1-3, wherein 2-Chloro-N-(2-dimethylaminoethyl)acetamide or a salt thereof is dissolved in an organic solvent.
5. The process of any one of embodiments 1-4, wherein the 2-Chloro-N-(2-dimethylaminoethyl) acetamide is a salt.
6. The process of any one of embodiments 1-5, wherein the aqueous base is NaOH.
7. The process of any one of embodiments 1-6, wherein the reaction takes place under an inert gas.
8. The process of any one of embodiments 1-7, wherein 1 molar equivalent 9-chloro-2,3-dimethyl-6H-Indolo [2,3-b] quinoxaline is deprotonized with at least 2 volumes of the aqueous base.
9. The process of embodiment 8, wherein 9-chloro-2,3-dimethyl-6H-Indolo[2,3-b] quinoxaline and the aqueous base are mixed at a suitable temperature until a clear solution is formed.
10. The process of any one of embodiments 2-9, wherein the catalyst in a suitable amount is added under vigorous stirring and mixed for 10 to 60 minutes at a suitable temperature.
11. The process of any one of embodiments 1-10, wherein 2-Chloro-N-(2-dimethylaminoethyl) acetamide or a salt thereof is added to the solution of 9-chloro-2,3-dimethyl-6H-Indolo[2,3-b] quinoxaline in the aqueous base and mixed for at least 1 hour at a suitable temperature.
12. The process of embodiment 11, wherein 2-Chloro-N-(2-dimethylaminoethyl) acetamide is added in an amount of 1-3.
13. The process of any one of embodiments 1-12, wherein Rabeximod is purified and isolated as the free base.
14. The process of embodiment 13, wherein Rabeximod is purified and isolated as a crystalline free base.
15. The process of any one of embodiments 1-14, wherein the process comprises the preceding step of:

reacting a solution or suspension of 4,5-Dimethyl-1,2-phenylenediamine with 5-chloroisatin under acidic conditions at elevated temperatures up to reflux to obtain 9-chloro-2,3-dimethyl-6H-Indolo[2,3-b] quinoxaline or a salt thereof.

16. The process of any one of embodiments 1-14, wherein the process comprises the preceding step of:

reacting a solution or suspension of Chloroacetyl chloride with N,N-Dimethylethylene diamine to obtain 2-Chloro-N-(2-dimethylaminoethyl)acetamide or a salt thereof.

17. The process of any one of embodiments 1-14, wherein the process comprises the preceding step of embodiment 15 and the preceding step of embodiment 16.
18. A process for preparing 9-chloro-2,3-dimethyl-6H-Indolo[2,3-b] quinoxaline wherein the process comprises the step of:

reacting a solution or suspension of 4,5-Dimethyl-1,2-phenylenediamine with 5-chloroisatin under acidic conditions at elevated temperatures up to reflux to obtain 9-chloro-2,3-dimethyl-6H-Indolo[2,3-b] quinoxaline.

19. The process of embodiment 15 or 18, wherein the acidic condition is an organic acid.
20. The process of any one of embodiments 15, 18 and 19, wherein 4,5-Dimethyl-1,2-phenylenediamine and 5-chloroisatin are both dissolved in the acid before the reaction.
21. The process of any one of embodiments 15 and 18-20, wherein the acid is in surplus.
22. The process of embodiment 15 or 21, wherein the acid is in at least 4 volumes surplus for 4,5-Dimethyl-1,2-phenylenediamine and at least 10 volumes surplus for 5-chloroisatin.
23. The process of any one of embodiments 15 and 18-22, wherein the elevated temperature is reflux temperature.
24. The process of any one of embodiments 15 and 18-23, wherein 4,5-Dimethyl-1,2-phenylenediamine or a salt thereof is dissolved in the acid before reaction with 5-chloroisatin and 5-chloroisatin or a salt thereof is dissolved in the acid before reaction with 4,5-Dimethyl-1,2-phenylenediamine.

25. The process of any one of embodiments 15 and 18-24, wherein 4,5-Dimethyl-1,2-phenylenediamine is added in an amount of 1-3 molar equivalents.
26. The process of any one of embodiments 15 and 18-25, wherein 5-chloroisatin is added in an amount of 1-3 molar equivalents.
27. The process of any one of embodiments 15 and 23-26, wherein dissolved 4,5-Dimethyl-1,2-phenylenediamine is added to dissolved 5-chloroisatin under reflux temperature.
28. The process of embodiment 15 or 27, wherein 4,5-Dimethyl-1,2-phenylenediamine is added to 5-chloroisatin over at least 2 hours under reflux temperature.
29. The process of any one of embodiments 15 and 27-28, wherein the acid is distilled from the reaction mixture and additional acid is added at a similar rate during the distillation.
30. The process of embodiment 15 or 29, wherein the reaction mixture, after distillation, is stirred at reflux temperature for at least 1 hour.
31. The process of any one of embodiments 15 and 18-30, wherein 9-chloro-2,3-dimethyl-6H-Indolo[2,3-b] quinoxaline is purified and isolated as the free base.
32. A process for preparing 2-Chloro-N-(2-dimethylaminoethyl) acetamide or a salt thereof wherein the process comprises the step of:

reacting a solution or suspension of Chloroacetyl chloride with N,N-Dimethylethylene diamine to obtain 2-Chloro-N-(2-dimethylaminoethyl)acetamide or a salt thereof.

33. The process of embodiment 16 or 32, wherein chloroacetyl chloride is dissolved in an organic solvent.
34. The process of any one of embodiments 16 and 32-33, wherein N,N-Dimethylethylene diamine is dissolved in an organic solvent.
35. The process of any one of embodiments 16 and 32-34, wherein Chloroacetyl chloride and N,N-Dimethylethylene diamine are both dissolved before the reaction.
36. The process of any one of embodiments 16 and 32-34, wherein N,N-dimethylethylene diamine in solution is added to Chloroacetyl chloride in solution at a rate keeping the temperature in the solution below 30° C.
37. The process of any one of embodiments 16 and 32-36, wherein N,N-dimethylethylene diamine or a salt thereof is dissolved in the solvent before reaction with Chloroacetyl chloride and 5 Chloroacetyl chloride or a salt thereof is dissolved in the solvent before reaction with N,N-dimethylethylene diamine.
38. The process of any one of embodiments 16 and 32-37, wherein the solvent is in surplus in relation to Chloroacetyl chloride such as at least about 2 volumes.
39. The process of any one of embodiments 16 and, 32-38, wherein the solvent is in equivalent or molar surplus in relation to N,N-Dimethylethylene diamine, such as in equivalent ratio.
40. The process of any one of embodiments 16 and, 32-39, wherein Chloroacetyl chloride is added in an amount of 1-3 molar equivalents.
41. The process of any one of embodiments 16 and, 32-40, wherein N,N-dimethylethylene diamine is added in an amount of 1-3 molar equivalents.
42. The process of any one of embodiments 16 and, 32-41, wherein 2-Chloro-N-(2-dimethylaminoethyl) acetamide or a salt thereof is purified and isolated as a salt thereof.
43. A crystalline free base of Rabeximod having a melting point of 259-261° C.
44. A crystalline free base of Rabeximod that is obtainable by the process as defined in any one of embodiments 1-17, 19-31 and 33-42.

EXPERIMENTAL

Figure 1:
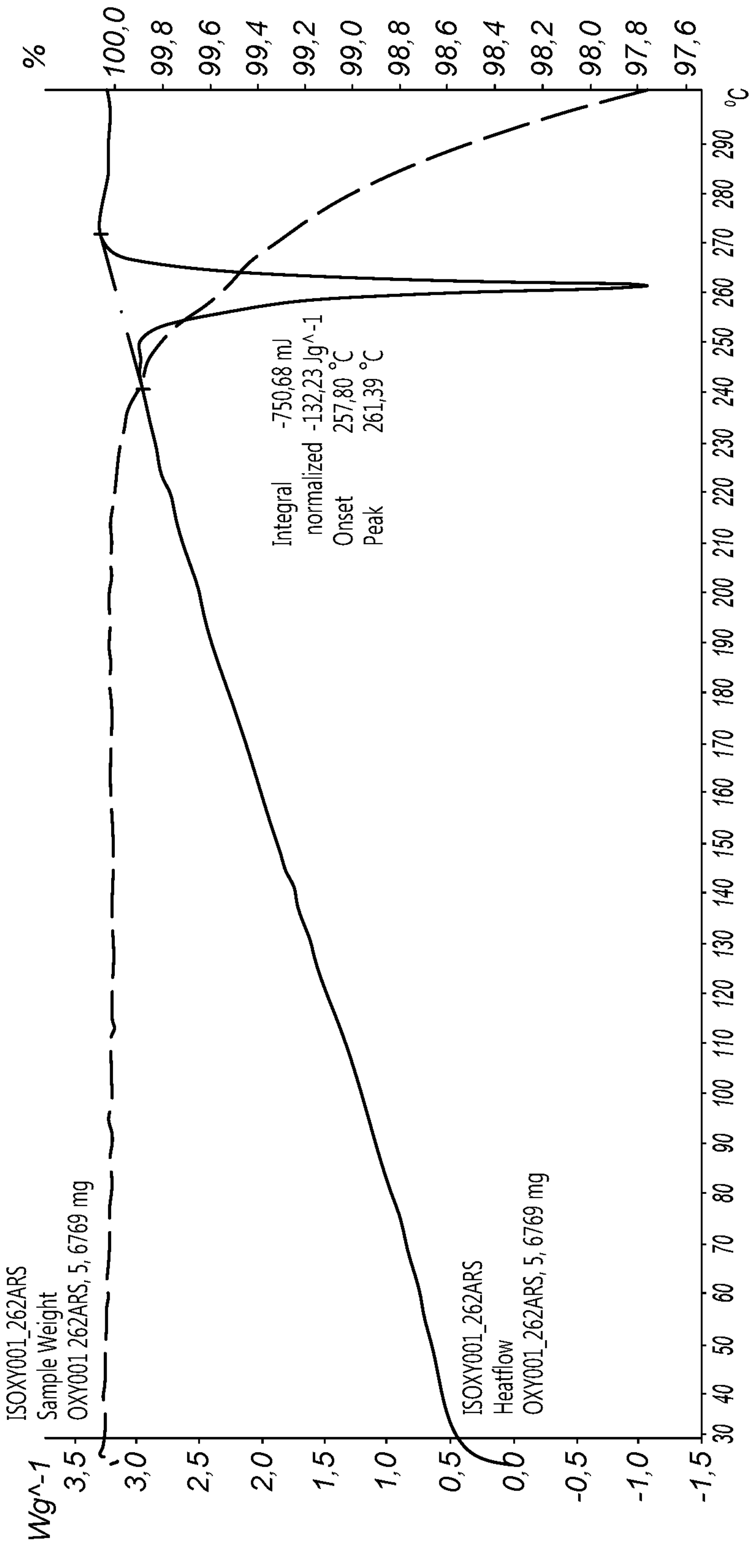
FIG. 1 shows the Differential scanning calometry (DSC) thermogram and Thermal gravimetric analysis (TGA) curve of Rabeximod.
Figure 2:
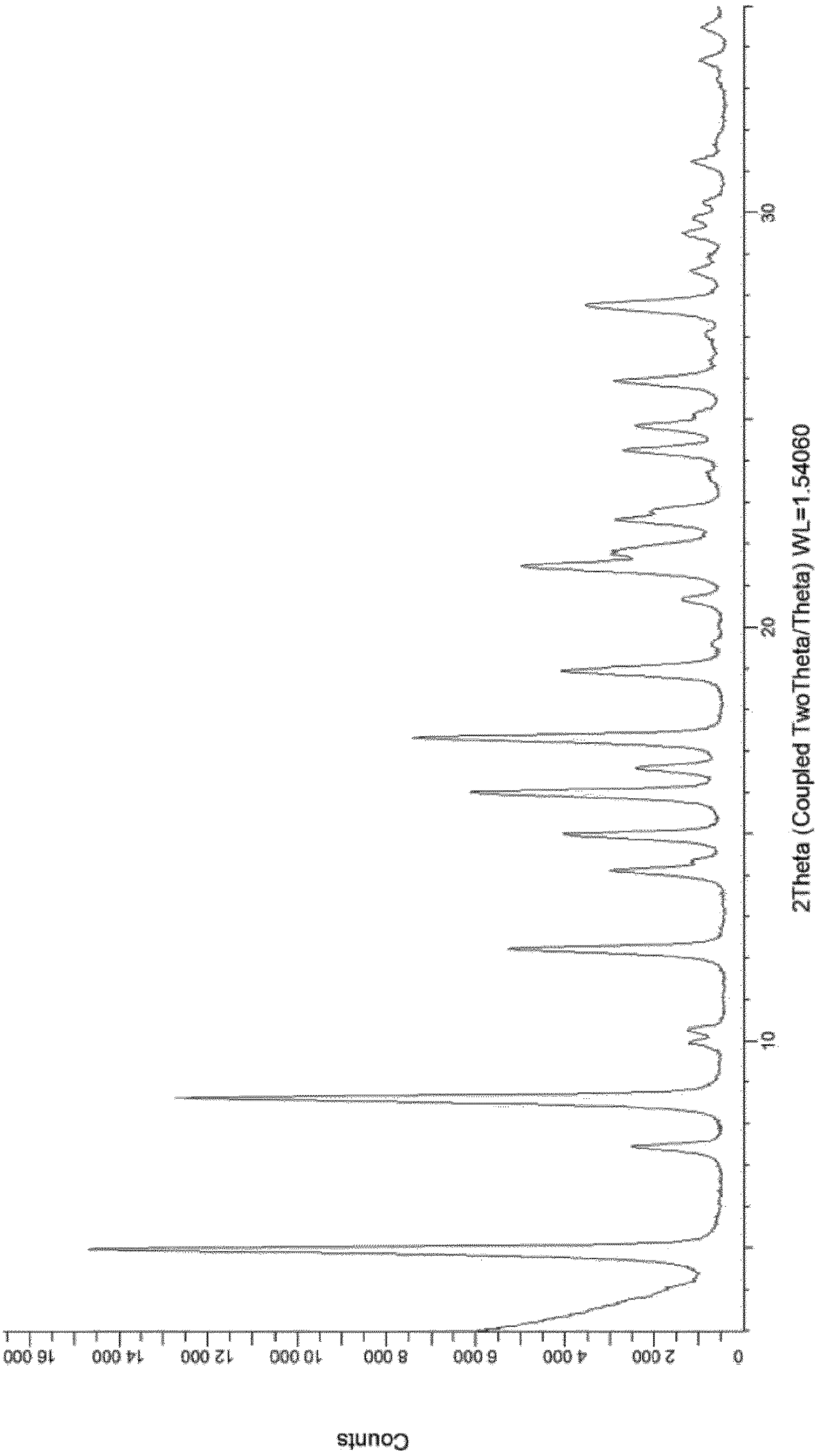
FIG. 2 shows the X-ray powder pattern of Rabeximod.

The current process to manufacture Rabeximod involves several process steps as illustrated in below reaction scheme and as described in detail hereunder.

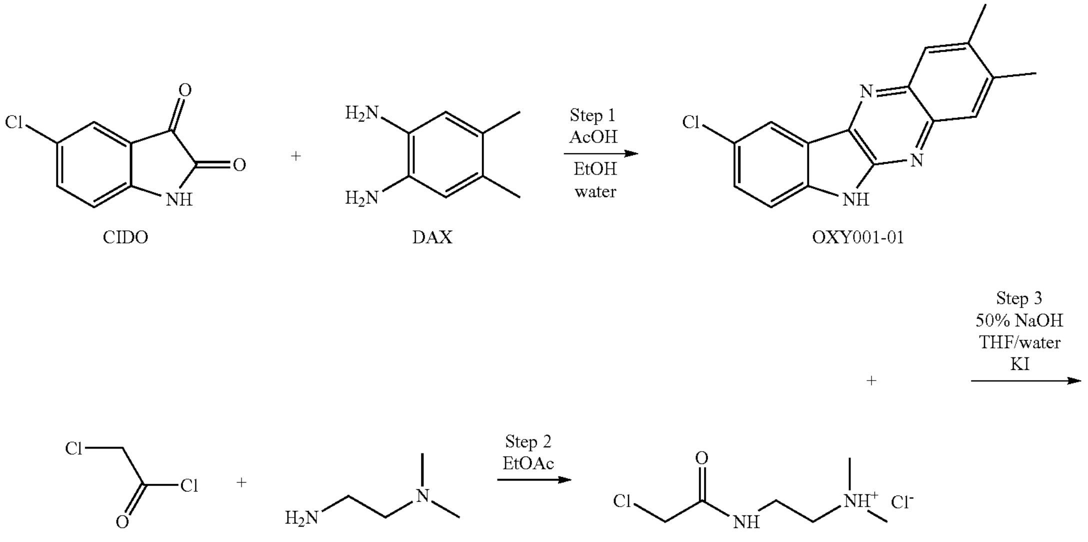

CIDO
DAX
OXY001-01
CAC
DMEN
OXY001-03 HCl

-continued

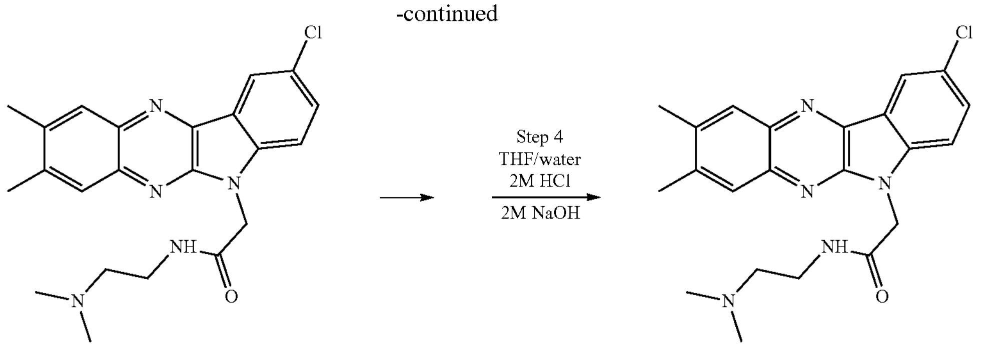

OXY001 crude

Manufacturing Process OXY001-01 Intermediate

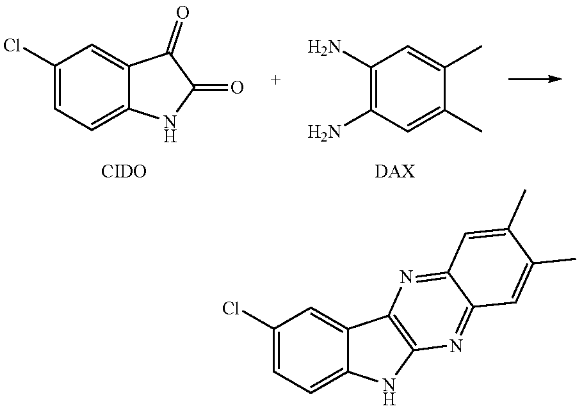

CIDO DAX

OXY001-01

Starting materials: 5-Chloroisatin (CIDO) and 4,5-Dimethyl-1,2-phenylenediamine (DAX)

TABLE 1

Overview Required Raw Materials and Quantities Step 1

| Item Description | MW | Mol | Quantity required | Eq. |
|---|---|---|---|---|
| 5-Chloroisatin (CIDO) | 181.58 | 66.1 | 12.0 kg | 1.0 |
| 4,5-Dimethyl-1,2-phenylene-diamine (DAX) | 136.19 | 72.7 | 9.9 kg | 1.1[a] |
| Acetic acid, AcOH | — | — | 282 L | 23.5[c] |
| Ethanol, EtOH | — | — | 150 L | 12.5[c] |
| Potable water | — | — | 50 | 4.2[c] |

[a]mol//mol of CIDO;
b) kg/kg of CIDO;
[c]L/kg of CIDO

TABLE 2

Raw Materials Specifications Step 1

| Item Description | Parameter | Method | Specification |
|---|---|---|---|
| 5-Chloroisatin (CIDO) | Appearance | Visual | Orange to brown powder |
| | ID | NMR | Conforms to structure |
| | Purity | GC | ≥95% |
| | Use Test | HPLC | ≥80% |

TABLE 2-continued

Raw Materials Specifications Step 1

| Item Description | Parameter | Method | Specification |
|---|---|---|---|
| 4,5-Dimethyl-1,2-phenylene-diamine (DAX) | Appearance | Visual | Off-white to brown powder |
| | ID | NMR | Conforms to structure |
| | Purity | GC | ≥95% |
| | Use Test | HPLC | ≥80% |
| Acetic acid, AcOH | Appearance | — | Colorless liquid from CoA |
| | ID | NMR/FITR | Conforms to reference |
| | Purity | — | ≥99% from CoA |
| Ethanol, EtOH | Appearance | Visual | Colorless liquid |
| | ID | NMR/FITR | Conforms to reference |
| | Purity | GC | >99.5% |

Resulting Product (Intermediate): OXY001-01

Batch size: 13.03 kg of OXY001-01

Process description: 4,5-Dimethyl-1,2-phenylenediamine (1.1 equivalent) was added to acetic acid (4.7 volumes) in reactor (reactor was running under nitrogen at atmospheric pressure) and stirred up to 3 hours at moderate rate at +20 to +25° C. until clear dark brown solution was formed. 4,5-Dimethyl-1,2-phenylenediamine solution in acetic acid solution was transferred to intermediate feeding vessel. 5-chloroisatin (1.0 equivalent) was added to acetic acid (14.3 volumes) in reactor and stirred while jacket temperature of reactor was adjusted to approximately +150° C. to achieve a reflux temperature for active reflux of solvents. When reflux temperature was reached the 4,5-Dimethyl-1,2-phenylenediamine solution in acetic acid was slowly added over 2-3 hours while distilling acetic acid (4.7 volumes) from the reaction mixture. A fresh portion of acetic acid (4.7 volumes) was added to the reactor at about the same rate as distillation (4.7 volumes) occurred. After distillation the reaction mixture was stirred at reflux temperature for at least another 2 hours. The expected appearance of content in the reactor was a dark yellow to orange slurry. The reaction mixture was cooled to +65 to +70° C. and filtered using a Nutsche filter using Polyester filter cloth (27 μm) or similar as filter media. The filter cake was washed 3 times with fresh ethanol (3×4.2 volumes) and 1 time with water (1×4.2 volume). After washing the filter cake was dried at +40 to +45° C. for 12 hours and additionally in a vacuum tray dryer for 12 hours at +40° C. resulting in a yellow to orange/brown solid. An in-process control sample was taken and analysed for loss on drying (LOD). LOD should be ≤2% (w/w). If the LOD is >2%, the vacuum tray dryer step was repeated.

Theoretical yield: 18.62 kg

Yield: 70±5% (13.03±0.96 kg)

Maximum volume: 216 L

Manufacturing Process OXY001-03 HCl Intermediate

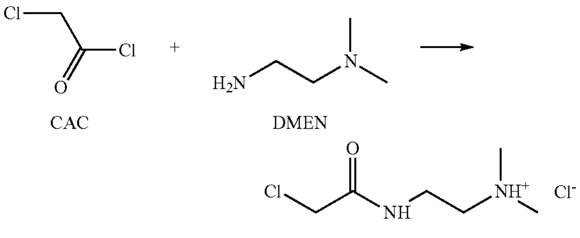

CAC

DMEN

OXY001-03 HCl

Starting materials: Chloroacetyl chloride (CAC) and N,N-Dimethylethylene diamine (DMEN)

TABLE 3

Overview Required Raw Materials and Quantities Step 2

| Item Description | MW | Mol | Quantity required | Eq. |
|---|---|---|---|---|
| N,N-Dimethylethylene diamine (DMEN) | 88.15 | 124.8 | 11.0 kg | 1.0 |
| Chloroacetyl chloride (CAC) | 112.94 | 128.5 | 14.5 kg | 1.03[a] |
| Ethyl acetate, EtOAc | — | — | 341 L | 31[c] |

[a]mol//mol of DMEN;
b) kg/kg of DMEN;
[c]L/kg of DMEN

TABLE 4

Raw Materials Specifications Step 2

| Item Description | Parameter | Method | Specification |
|---|---|---|---|
| N,N-Dimethylethylene diamine (DMEN) | Appearance | Visual | Clear colorless to yellow liquid |
| | ID | NMR | Conforms to reference |
| | Purity | GC | ≥95% |
| Chloroacetyl chloride (CAC) | ID | — | Correct product from CoA |
| | Purity | — | ≥95% from CoA |
| Ethyl acetate, EtOAc | Appearance | — | Colorless liquid |
| | ID | NMR or FTIR | Conforms to reference |
| | Purity | — | ≥99% from CoA |

Resulting Product (Intermediate): OXY001-03 HCl

Batch size: 22.6 kg of OXY001-03 HCl

Process description: Chloroacetyl chloride (1.03 equivalents) was dissolved in ethyl acetate (15 volumes) in reactor (reactor was running under nitrogen at atmospheric pressure) at +20° C. The solution was stirred and cooled down to +10° C. N,N-dimethylethylene diamine (1.00 equivalent) solution in ethyl acetate (1.0 volume) was slowly charged to the reactor when the temperature reached a range from +10 to +25° C. and at such a rate over 1-2 hours that the internal temperature did not exceed +25° C. The slurry was stirred for 5 to 30 minutes at +20 to +25° C. and filtered using a Nutch filter using Polyamide filter cloth (25 μm) or similar as filter media. The product was washed 3 times on the filter with ethyl acetate (3x5 volumes) and dried on the filter for at least 16 hours and additionally in a vacuum tray dryer for 12 hours at +40° C. resulting in an off-white to beige solid.

Theoretical yield: 25.09 kg

Yield: 90±5% (22.6±1.25 kg)

Maximum volume: 202 L

Manufacturing Process OXY001 Crude

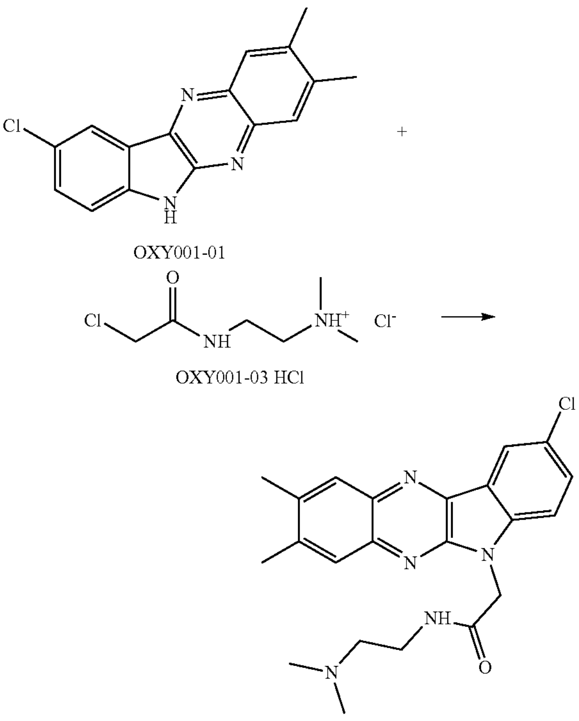

OXY001-01

OXY001-03 HCl

OXY001 Crude

Starting materials: OXY001-01 and OXY001-03 HCl

TABLE 5

Overview Required Raw Materials and Quantities Step 3

| Item Description | MW | Mol | Quantity required | Eq. |
|---|---|---|---|---|
| OXY001-01 | 281.74 | 46.3 | 13.0 kg | 1.0 |
| OXY001-03 HCl | 201.09 | 92.5 | 18.6 kg | 2.0[a] |
| 50% NaOH aq. solution | 40.00 | 370.1 | 29.6 kg | 8.0[a] |
| Potassium iodide, KI | 166.00 | 37.5 | 6.2 kg | 0.81[a] |
| Tetrahydrofuran, THF | — | — | 705 L | 54.2[c] |
| Potable water | — | — | 395 L | 30.4[c] |

[a]mol//mol of OXY001-01;
b) kg/kg of OXY001-01;
[c]L/kg of OXY001-01

TABLE 6

Raw/Intermediate Materials Specifications Step 3

| Item Description | Parameter | Method | Specification |
|---|---|---|---|
| OXY001-01 | Appearance | Visual | Yellow to orange/ brown solid |
| | ID | NMR | Conforms to structure |
| | Purity | HPLC | ≥80% |
| | Use test | HPLC | ≥98% of OXY001 |
| OXY001-03 HCl | Appearance | Visual | White to off-white solid |
| | ID | NMR | Conforms to structure |
| | Residual EtOAc | NMR | To be reported |
| | Purity | GC | ≥90% |

TABLE 6-continued

| Raw/Intermediate Materials Specifications Step 3 | | | |
|---|---|---|---|
| Item Description | Parameter | Method | Specification |
| 50% NaOH aq. solution | Appearance | Visual | Colorless liquid |
| | ID | pH at 25° C. | 12-14 |
| | Assay | — | >31 w/w % from CoA |
| Potassium iodide, KI | Appearance | Visual | Colorless to white solid |
| | ID | EP | Conforms |
| | Assay by titration | — | ≥95% from CoA |
| Tetrahydrofuran, THF | Appearance | Visual | Colorless liquid |
| | ID | NMR | Conforms to reference |
| | Purity | GC | ≥99% |

Resulting Product: OXY001 Crude (crude rabeximod)

Batch size: 11.38 kg of OXY001 Crude

Process description: OXY001-01 (1.0 equivalent) was dissolved in tetrahydrofuran (15.4 volumes) and 50% NaOH aqueous solution (8.0 equivalents in relation to OXY001-01) in reactor (reactor was running under nitrogen at atmospheric pressure) and mixed at +55 to +60° C. up to approximately 1 hour until clear dark red solution was formed. Potassium iodide (0.81 equivalents) was added under vigorous stirring and mixed for 10 to 30 minutes at +55 to +60° C. OXY001-03 HCl (2.0 equivalents) was added to the solution and mixed for at least 2 hours at +55 to +60° C. Following completion of the reaction, the mixture was quenched with water (15.4 volumes) and tetrahydrofuran removed (15.4 volumes) by evaporation under reduced pressure. The slurry was cooled to +20 to +25° C. and stirred for 1 hour and filtered with a Nutch filter using Polyamide filter cloth (25 μm) or similar as filter media. Resulting cake was washed 3 times with water (3×5 volumes) until the pH of the filtrate was between 8-7 and dried on the filter at +40 to +45° C. for at least 12 hours by air suction and additionally in a vacuum tray dryer for 12 hours at +40° C. Afterwards resulting material was suspended in in tetrahydrofuran (25 volumes) at +45 to +50° C. for at least 1 hour. OXY001 Crude was isolated by filtration with a Nutch filter using Polyamide filter cloth (25 μm) or similar as filter media and washed 2 times on the filter with tetrahydrofuran (2×7 volumes). Resulting cake was dried on the filter at +40 to +45° C. for at least 12 hours and additionally in a vacuum tray dryer for 12 hours at +40° C.

Theoretical yield: 18.96 kg

Yield: 60±5% (11.38±0.95 kg)

Maximum volume: 500 L

Purification of Crude Rabeximod:

OXY001 crude (1.0 equivalent) was dissolved in tetrahydrofuran (10 volumes), water (3 volume), and 2M HCl (1.4 volumes) mixture. The solution was clear filtered and heated to +50° C. pH of mixture was adjusted to 10-12 by addition of 2M NaOH (1.3 volume). The formed slurry was cooled to +20 to +25° C. and diluted with water (12 volumes).

After stirring for at least 12 hours the slurry was filtered at +20 to +25° C. and washed on the filter with tetrahydrofuran:water (5:2) mixture (2×3 volumes). Rabeximod has a molecular weight of 409.92 g/mol and is isolated as a crystalline free base having a melting point of 259-261° C.

Batch release results of batches used in Phase 2 and Phase 1 clinical studies are provided in Table 7.

Purity is equal to or above 98% as measured by HPLC.

TABLE 7

Batch release results of Rabeximod drug substance batches used in Phase 1 and phase 2 clinical studies

| Batch Size (kg)<br>Use<br>Test | Acceptance Criteria | 7.1<br>Phase 2<br>Clinical | 6<br>Nonclinical, Stability, Phase 1<br>Clinical |
|---|---|---|---|
| Appearance | Yellow powder | Yellow powder | Conforms |
| Identification (IR) | Conforms to reference spectrum | Conforms to reference spectrum | Conforms |
| Chromatographic purity (HPLC) | ≥98 area-% | 99.7% | 99.8 area-% |
| Residual solvents (GC) | | | |
| Tetrahydrofuran | ≤720 ppm | 492 ppm | <720 ppm |
| Heavy metals | ≤10 ppm | ≤10 ppm | <10 ppm |
| Microbiological quality | | | |
| Total plate count | $\leq 10^2$ CFU/g | <5 CFU/g | <10 CFU/g |
| *E. coli* | Absence in 1 g | Negative | Negative |
| Assay (titration) | 95-105 w/w % | 99.3% | 99.0 w/w % |
| Related substances | | | |
| Largest impurity | ≤1.0 (area %) | 0.05 | 0.1 area-% |
| Number of impurities >0.05 area-% | To be reported | 1 (RRT 0.82) | 3 |
| Sum of impurities >0.1% | ≤2.0 (area %) | 0 | 0.1 area-% |
| Residual OXY001-03 (GC) | ≤0.2 (% w/w) | <0.03% | Not Tested |
| Assay (HPLC) | 95-105 (% w/w) | 99.9% | 99.3% |
| Water content (KF) | To be reported (% w/w) | 0.1% | 0.1 w/w % |
| Loss on drying | To be reported (% w/w) | <0.1% | 0.1 w/w % |
| Sulphated Ash | To be reported (% w/w) | <0.1% | 0.1 w/w % |

The invention claimed is:

1. A process for preparing 9-chloro-2,3-dimethyl-6-(N,N-dimethylaminoethylamino-2-oxoethyl)-6H-indolo-[2,3-b] quinoxaline (rabeximod) or a salt thereof, wherein the process comprises the step of:

reacting a solution or suspension of 9-chloro-2,3-dimethyl-6H-indolo[2,3-b]quinoxaline in the presence of an aqueous base sufficiently strong to deprotonize the indole N—H, with 2-chloro-N-(2-dimethylaminoethyl) acetamide or a salt thereof to obtain rabeximod or a salt thereof.

2. The process of claim 1, wherein a catalyst is present in the solution or suspension.

3. The process of claim 1, wherein 9-chloro-2,3-dimethyl-6H-indolo[2,3-b]quinoxaline or a salt thereof is dissolved in an organic solvent and wherein 2-chloro-N-(2-dimethylaminoethyl) acetamide or a salt thereof is dissolved in an organic solvent.

4. The process of claim 1, wherein the aqueous base is NaOH.

5. The process of claim 1, wherein 1 molar equivalent 9-chloro-2,3-dimethyl-6H-indolo[2,3-b]quinoxaline is deprotonized with at least 2 volumes of the aqueous base and wherein 9-chloro-2,3-dimethyl-6H-indolo[2,3-b]quinoxaline and the aqueous base are mixed at a suitable temperature until a clear solution is formed.

6. The process of claim 2, wherein the catalyst in a suitable amount is added under vigorous stirring and mixed for 10 to 60 minutes at a suitable temperature.

7. The process of claim 1, wherein 2-chloro-N-(2-dimethylaminoethyl) acetamide or a salt thereof is added to the solution of 9-chloro-2,3-dimethyl-6H-indolo[2,3-b]quinoxaline in the aqueous base and mixed for at least 1 hour at a suitable temperature.

8. The process of claim 1, wherein rabeximod is purified and isolated as a crystalline free base.

9. The process of claim 1, wherein the process comprises the preceding step of:

reacting a solution or suspension of 4,5-dimethyl-1,2-phenylenediamine with 5-chloroisatin under acidic conditions at elevated temperatures up to reflux to obtain the 9-chloro-2,3-dimethyl-6H-indolo[2,3-b]quinoxaline or a salt thereof.

10. The process of claim 1, wherein the process comprises the preceding step of:

reacting a solution or suspension of chloroacetyl chloride with N,N-dimethylethylene diamine to obtain the 2-chloro-N-(2-dimethylaminoethyl) acetamide or a salt thereof.

11. The process of claim 1, wherein the process comprises the preceding steps of reacting a solution or suspension of 4,5-dimethyl-1,2-phenylenediamine with 5-chloroisatin under acidic conditions at elevated temperatures up to reflux to obtain 9-chloro-2,3-dimethyl-6H-indolo[2,3-b]quinoxaline or a salt thereof; and reacting a solution or suspension of chloroacetyl chloride with N,N-dimethylethylene diamine to obtain 2-chloro-N-(2-dimethylaminoethyl) acetamide or a salt thereof.

12. The process of claim 9, wherein the acidic condition is an organic acid.

13. The process of claim 9, wherein 4,5-dimethyl-1,2-phenylenediamine and 5-chloroisatin are both dissolved in the acid before the reaction.

14. The process of claim 9, wherein the elevated temperature is reflux temperature.

15. The process of claim 11, wherein the acidic condition is an organic acid.

16. The process of claim 11, wherein 4,5-dimethyl-1,2-phenylenediamine and 5-chloroisatin are both dissolved in the acid before the reaction.

17. The process of claim 11, wherein the elevated temperature is reflux temperature.

* * * * *